(12) United States Patent
Tureci et al.

(10) Patent No.: US 6,214,983 B1
(45) Date of Patent: Apr. 10, 2001

(54) ISOLATED NUCLEIC ACID MOLECULES WHICH ENCODE SCP PROTEINS

(75) Inventors: Ozlem Tureci; Ugur Sahin; Michael Pfreundschuh, all of Homburg/Saar (DE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/177,325

(22) Filed: Oct. 22, 1998

(51) Int. Cl.[7] ............................. C07H 21/02; C12Q 1/68
(52) U.S. Cl. ................................. 536/23.2; 435/6
(58) Field of Search .................. 536/23.2; 435/6

(56) References Cited

U.S. PATENT DOCUMENTS 5,888,751 * 3/1999 Tureci et al. ...................... 438/7.23

OTHER PUBLICATIONS

Offenberg, et al, "SCP2: a major protein component of the axial elements of synaptonemal complexes of the rat" Nucleic Acids Research, 1998, vol. 26, No. 11:2572–2579.*
Worley, K.C. GenCore, 1997.*
Hillier, et al GenCore, 1997.*
NCI–CGAP GenCore, 1997.*
Stuhlmueller, et al GenCore 1996.*
Worley, KC GenCore, 1997.*

* cited by examiner

*Primary Examiner*—Eggerton A. Campbell
(74) *Attorney, Agent, or Firm*—Fulbright & Jaworski, LLP

(57) ABSTRACT

The invention involves the recognition of a previously unidentified protein family which belongs to, the human SCP family. The members of the family, such as SCP-2 and rat SCP-3 homolog are markers for cell transformation. Diagnostic and therapeutic uses of these protein and related molecules are taught.

8 Claims, No Drawings

ISOLATED NUCLEIC ACID MOLECULES WHICH ENCODE SCP PROTEINS

FIELD OF THE INVENTION

The invention relates to the identification of a molecule or a marker for transformed cells, such as cancer. It also relates to a method for identifying molecules associated with pathological conditions, such as cancer.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding nucleic acid molecule to express the desired protein molecule.

To date, two strategies have been employed for the detection of such antigens, in e.g., human tumors. These will be referred to as the genetic approach and the biochemical approach. The genetic approach is exemplified by, e.g., dePlaen et al., Proc. Natl. Sci. USA 85: 2275 (1988), incorporated by reference. In this approach, several hundred pools of plasmids of a cDNA library obtained from a tumor are transfected into recipient cells, such as COS cells, or into antigen-negative variants of tumor cell lines. Transfectants are screened for the expression of tumor antigens via their ability to provoke reactions by anti-tumor cytolytic T cell clones. The biochemical approach, exemplified by, e.g., Mandelboim, et al., Nature 369: 69 (1994) incorporated by reference, is based on acidic elution of peptides which have bound to MHC-class I molecules of tumor cells, followed by reversed-phase high performance liquid chromatography (HPLC). Antigenic peptides are identified after they bind to empty MHC-class I molecules of mutant cell lines, defective in antigen processing, and induce specific reactions with cytotoxic T-lymphocytes. These reactions include induction of cytolytic T cell lines (CTLS) proliferation tumor necrosis factor (TNF) release, and lysis of target cells, measurable in an MTT assay, or a $^{51}$Cr release assay.

These two approaches to the molecular definition of antigens have the following disadvantages: first, they are enormously cumbersome, time-consuming and expensive; second, they depend on the establishment of CTLs with predefined specificity; and third, their relevance in vivo for the course of the pathology of disease in question has not been proven, as the respective CTLs can be obtained not only from patients with the respective disease, but also from healthy individuals, depending on their T cell repertoire.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643–1647(1991); Richard et al., J. Exp. Med. 178: 489–495 (1993); Coulie, et al., J. Exp. Med. 180: 35–42 (1994); Kawakami, et al., Proc. Natl. Acad. Sci. USA 91: 3515–3519 (1994).

Further, the methodologies supra described rely on the availability of established, permanent cell lines of the cancer type under consideration. It is very difficult to establish cell lines from certain cancer types, as is shown by, e.g., Oettgen, et al., Immunol. Allerg. Clin. North. Am. 10: 607–637 (1990). It is also known that some epithelial cell type cancers are poorly susceptible to CTLs in vitro, thus precluding routine analysis. These problems have stimulated the art to develop additional methodologies for identifying cancer associated antigens.

One key methodology is described by Sahin, et al., Proc. Natl. Acad. Sci. USA 92: 11810–11913 (1995), incorporated by reference. Also, see U.S. Pat. No. [5410], and application Ser. No. 08/479,328, filed on Jun. 7, 1995 and Jan. 3, 1996, respectively. All three of these references are incorporated by reference. To summarize, the method involves the expression of cDNA libraries in a prokaryotic host. (The libraries are secured from a tumor sample). The expressed libraries are then immunoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., supra, as well as Crew, et al., EMBO J 144: 2333–2340 (1995).

The SEREX methodology has been applied to esophageal cancer samples, and an esophageal cancer associated antigen has now been identified, and its encoding nucleic acid molecule isolated and cloned, as per U.S. patent application Ser. No. 08/725,182, filed Oct. 3, 1996, incorporated by reference herein.

The relationship between some of the tumor associated genes and a triad of genes, known as the SSX genes, is under investigation. See Sahin, et al., supra; and Tureci, et al., Cancer Res 56:4766–4772 (1996). One of these SSX genes, referred to as SSX2, was identified, at first, as one of two genes involved in a chromosomal translocation event (t(X; 18)(p 11.2; q 11.2)), which is present in 70% of synovial sarcomas. See Clark, et al., Nature Genetics 7:502–508 (1994); Crew et al., EMBO J 14:2333–2340 (1995). This gene was later found to be expressed in a number of tumor cells, and is now considered to be a tumor associated antigen referred to as HOM-MEL-40 by Tureci, et al, supra. Its expression to date has been observed in cancer cells, and normal testis only. This parallels other members of the "CT" family of tumor antigens, since they are expressed only in cancer and testis cells. Crew et al. also isolated and cloned the SSX1 gene, which has 89% nucleotide sequence homology with SSX2. See Crew et al., supra. Additional work directed to the identification of SSX genes has resulted in the identification of SSX3, as is described by DeLeeuw, et al., Cytogenet. Genet 73:179–183 (1996). The fact that SSX presentation parallels other CT antigens suggested to the inventors that other SSX genes might be isolated.

Application of a modification of the SEREX technology described supra has been used, together with other techniques, to clone two, additional SSX genes, referred to as SSX4 and SSX5 as alternate splice variants of the SSX4 gene. This work is described in U.S. Ser. No. 08/851,138, filed May 5, 1997, incorporated by reference, as well as by Chen, et al., Proc. Natl. Acad. Sci USA 94: 1914–1918 (1997), also incorporated by reference.

The fact that many markers were found in both normal testis and tumor cells, but not other normal cells, suggested that further investigation in this area might uncover additional related molecules. The diversity of those discovered so far, however, did not provide any guidance as to the characteristics of the additional molecules which might be found.

Most of the work prior to the invention disclosed herein, used cDNA libraries obtained from cancer cells. As will be developed herein, it has now been shown that such molecules can also be determined using a non-transformed, or normal cell source for the cDNA libraries previously obtained from cancer cells. This is quite surprising, as it might well be assumed that tumor markers are expressed only in tumor cells. This has now been shown to not be the case. Exemplary of a normal cell library which can be used is a testis cell library screened against various serum samples, such as autologous serum.

Synaptonemal complex protein 1 ("SCP1" hereafter) is a protein involved in the meiotic prophase of spermatocytes. The gene which encodes murine SCP1 has been mapped to chromosome 1p.12–p.13. See Sage, et al, Biochem. Biophys. Acta 1263: 258–260 (1995) incorporated by reference. The human form of SCP1 has been reported to be expressed only in testis. See Meuwissen, et al, EMBO J 11:5091–5100 (1992), incorporated by reference.

Meuwissen et al, supra describe SCP1 protein as a major component of the synaptonemal complex, a tripartite, macromolecular assembly which is formed between homologous chromosomes during meiotic prophase. See Wettstein, et al, Annu. Rev. Genet 3:331–413 (1984); Heyting, et al, Genome 31:81–89 (1986). More details of the protein may be found e.g., in Meuwissen, et al, Genomics 37:101–106 (1997); Gillies, et al, Curr. Trac. Lab. Carlsberg 40:135–161 (1975); Schmekel, et al, Exp. Cell Res 226:20–30 (1996); Moses, et al, Symp. Soc. Exp. Biol. 38:245–270 (1984); Carpenter, Bioessays 6:232–236 (1987); Loidl, et al, Genome 33:759–778 (1990); Moens, Bioessays 16:101–106 (1994); Roeder, Trends Genet 6:385–389 (1990).

The location of the gene for SCP1 is different than that for all previously identified cancer testis antigens (CTAs), which map to the X chromosome.

In allowed U.S. application Ser. No. 08/892,702, filed Jul. 15, 1997 now U.S. Pat. No. 5,888,751, and incorporated by reference, it was shown that SCP1 is expressed in tumor cells, especially in renal cell carcinomas, gliomas, and breast carcinomas, but not in normal cells except for testis. Hence, it serves as a CTA but differs in that it possesses strong expression not only in melanoma, but in those tumor types listed supra.

This is significant in terms of both diagnostic and therapeutic approaches to transformed cells, as will be seen from the disclosure which follows. The fact that the molecule is also involved in normal meiosis suggested an important correlation between the molecule, chromosomal replication, cell division, and the onset of oncogenesis.

The SCP1 gene was found to be testis specific, in that the only normal cells in which it was expressed were testis. Additional research has now been carried out, and additional isolated nucleic acid molecules have been identified which serve as cancer markers, but the only normal cells in which they are expressed are testis cells. More detailed information on these molecules and their use is set forth in the disclosure which follows.

DETAILED DESCRIPTION OF PREFERRED EMBODIMENTS

EXAMPLE 1

An electronic search of the Genbank database was carried out to identify known nucleic acid molecules which belong to the synaptonemal complex described supra. Specifically, the search criteria were testis specific expression, and association with meiosis. The result of this search yielded a non-homologous sequence, for rat SCP3. No human counterpart was found; however, a rat SCP3 sequence was identified, and was then used to search for homologous sequences in the human expression sequence tag ("EST") databases. Two sequences were identified. The search was a BLAST search of the DBEST database. "BLAST" is an acronym for Basic Local Alignment Search Tool. DBEST is a database of EST sequences. These have access numbers AA431205 and AA431529 in the sequence libraries. Both were reported as having come from a testis library. These publicly available sequences are incorporated by reference.

The AA431205 sequence was used to design a primer for RACE analysis in accordance with Frohman, et all, Meth. Enzymol 218: 340–356 (1993), incorporated by reference. Two rounds of RACE were carried out, using an anchor primer and ACAGAAGTGT CTAGGATTCA TTCA SEQ ID NO:5 (round 1), then the anchor primer and GACAGAGGAG CTATACCGAT TTATAC SEQ ID NO:15. The primer was used to screen a testicular library, and two transcripts were identified. These are referred to as SEQ ID NO: 1 (SCP3A), and SEQ ID NO: 2 (SCP3B) hereafter. These sequences were then compared to sequences in the genbank library, using BLAST. Two highly homologous sequences were identified, referred to as gbAC 002366 and gbAC 003046. Both of these are sequences reported by the human genome project, as coming from human chromosome X. The former is a cosmid from region Xp22, while the latter is a PAC from Xp22 RPC11-263P4. Both of these library items represent genomic DNA sequences. Using exon/intron determination rules, SEQ ID NOS: 3 and 4 were determined, as being expressed or translated portions. The former corresponds to the 3'-end of a gene homologous to SEQ ID NOS: 1 and 2, while the latter sets forth an entire gene sequence which is homologous to SEQ ID NOS: 1 and 2 as well.

EXAMPLE 2

The information from AA431205, which was 518 base pairs long was used to study expression in normal and cancer tissues. Two oligonucleotide primers were prepared, based upon the sequence information, and were used in assays, described infra.

The oligonucleotide primers were:

ACAGAAGTGT CTAGGATTCA TTCA (SEQ ID NO: 5, sense) and

GAAGAGGTGG CAACAATAT AG (SEQ ID NO: 6 antisense), respectively.

RT-PCR was then carried out, using these primers, for 35 cycles (one cycle: (60° C. for one minute, 72° C. for two minutes, 94° C. for one minute), preceded by 12 minutes at 94° C. followed by a final "cycle" of 72° C. for 8 minutes.

No expression was found in any normal tissue tested except testis; however, PCR product was found in prostate, breast, ovarian, and renal cell carcinoma cancer tissues.

In addition to products of the expected size, aberrant smaller products were found in breast cancer samples. One of these aberrant clones was sequenced, and the sequence is set forth at SEQ ID NO: 7. While different from all of SEQ ID NOS: 1, 2, 3, and 4, it is related to these sequences.

EXAMPLE 3

In experiments not reported here, it was found that of normal tissue samples, only testis was positive for any of the sequences under consideration. In addition to SEQ ID NOS: 5 & 6, which were used to analyze for SEQ ID NO: 1, primers:

5'-ACCTACAGGT GTTAGGAGCT G-3'(SEQ ID NO: 8) and

5'-ACAGAGGTTG TTGAGACAAT G-3'(SEQ ID NO: 9)

were used, as sense and antisense to determine SEQ ID NO: 2. The RT-PCR for analyzing the samples involved 12 minutes of denaturing, followed by 35 cycles of 1 minute at 60° C., 2 minutes at 72° C., and 1 minute at 94° C., followed by 35 cycles of 1 minute at 94° C.

The samples which were negative included stomach, muscle, colon, lung, breast, liver, prostate, kidney, skin, and brain.

EXAMPLE 4

The RT-PCR protocols given supra were then used, with SEQ ID NOS: 5&6 or 10&11, to determine expression in cancer. The results are as follows, expressed as "x/y", where "x" is the number of positive samples, and "y" is the total number analyzed. SEQ ID NO: 4 was detected using:

5'GCAGAAACGT GATTATAGAA-T-3'(SEQ ID NO: 10) and

5'-GGTTGAAGAT ACATCTGAAT A-3'(SEQ ID NO: 11)

| CANCER TYPE | SEQ ID NO: 1 | SEQ ID NO: 4 |
|---|---|---|
| Prostate | 4/26 | 0/26 |
| Renal Carcinoma | 2/23 | 1/15 |
| Melanoma | 4/18 | 3/12 |
| Melanoma Cell Lines | 1/5 | not done |
| Ovarian | 0/25 | 6/25 |
| Breast | 0/10 | 2/15 |
| Colorectal | 0/10 | 0/10 |
| Lung | 0/8 | 0/8 |

When the primers and conditios of example 3 were used, SEQ ID NO: 7 was found in breast cancer.

EXAMPLE 5

The work set forth supra deals with human nucleic acid molecules with homology to rat SCP3. Recently Offenburg et al., Nucl. Acids, Res. 26(11): 2572–2579 (1998), the disclosure of which is incorporated by reference, disclosed human SCP2. This sequence is presented as SEQ ID NO: 12. It is publicly available via genbank accession number 708982, incorporated by reference. As with SCP1 and SCP3, the SCP gene was described as being expressed specifically in testis, but was not associate with cancer.

Following study of the SCP2 sequence, primers were designed for RT-PCR. These were:

5'-GATTCGGCAC GCAGGGGATG TTATACC-3'(SEQ ID NO: 13) and

5'-GCCAATCACT CTGCTTGGCA TTTTCAG (SEQ ID NO: 14)

which served as sense, and antisense primers, respectively.

RT-PCR was carried out in total cellular RNA which had been extracted, and screened with oligos, and then reverse transcribed.

The PCR was carried out by heating the cDNA for 2 minutes at 95° C., followed by 35 cycles of 1 minute at 60° C., 2 minutes at 72° C., and one minute at 94° C.

The RT-PCR was carried out on normal stomach, muscle, colon, lung, breast, liver, prostate, kidney, skin, brain and testis tissues. Only testis was positive.

Tumor samples were also analyzed. The results follow expressed as "x/y", where "x" is the number of positive samples, and "y" the total number tested:

| CANCER TYPE | |
|---|---|
| Ovarian | 1/5 |
| Breast | 3/15 |
| Melanoma | 2/8 |
| Glioma | 12/28 |
| Leukemia | 6/20 |
| Colorectal | 0/10 |
| Renal | 0/5 |
| Prostate | 0/10 |
| Stomach | 0/10 |
| Bronchial | 0/10 |

The foregoing examples demonstrate several features of the invention. These include isolated nucleic acid molecules which have complementary sequences that hybridize to at least one of SEQ ID NOS: 1, 2, 4 and 7 under stringent conditions. In a preferred embodiment, these isolated nucleic acid molecules encode human SCP2 or SCP3. Stringent conditions refer to conditions at least as stringent as overnight hybridization in 5×SSC buffer, including 2×Denhard's solution, using a 300 base pair $^{32}$P labelled probe (20 ng/ml of solution) at 65° C., followed by 2 washes of 15 minutes each, using 1×SSC per wash. Also a part of the invention are expression vectors which comprise any of the foregoing sequences, operably linked to a promoter. Such expression vectors, as well as the isolated nucleic acid molecules themselves, may be used to produce recombinant eukaryotic or prokaryotic cells, which have been transformed or transfected with the isolated nucleic acid molecules or expression vectors of the invention. Also a part of the invention are diagnostic methods for determining presence of transformed cells, such as cancer cells, in a sample. The examples show that there is a family of SCP genes which are expressed in cancer cells. Hence, the invention involves, inter alia, detecting protein encoded by the nucleic acid molecules or mRNA such as those described in a sample taken from a source other than testis, wherein presence of either or both of these is indicative of a pathology, such as cancer or some other type of transformed cells. Exemplary of the type of diagnostic assays which can be carried out are amplification assays such as polymerase chain reaction, or immunoassays. It is especially preferred to assay for a determination of prostate cancer, breast cancer, melanoma, ovarian cancer, renal cell carcinoma, or glioma. Preferably, the oligonucleotides of SEQ ID NOS: 5, 6, 8, 9, 10, 11, 13 or 14 are used. Any sequence which hybridizes to SEQ ID NO: 1, 2, 4, 7 or 12 ('205), can be used.

The SCP proteins, as indicated, have been associated, exclusively, with meiosis. As a rule, cells other than germ cells do not undergo meiosis. Hence, the expression of SCP proteins such as SCP-3 in a context other than germ cells undergoing meiosis is clearly an indication of an abnormality. It is believed that expression of SCP proteins such as SCP-3 may contribute to the genetic instability of cancer cells, leading to abnormalities such as aneuploidy, manifesting the phenomenon in early neoplastic change. One aspect of the invention, then, is a method for determining presence of an abnormal condition by assaying for an SCP protein, or a peptide derived from the protein, wherein the presence of the protein at all, or an abnormal level of the protein (which may include its presence), is indicative of an abnormality, such as cancer. There are many ways to carry out this type of assay. For example, as indicated herein, antibodies to the protein were found in patient samples. One can assay for these antibodies using, e.g., the methodology described herein, or by using a purified SCP protein or antigenic fragment thereof, and so forth. One can also assay for the protein itself, using antibodies, which may be isolated from samples, or generated using an SCP protein and standard techniques. This antibodies can then be labelled, if desired, and used in standard immunoassays.

Similarly, any and all nucleic acid hybridization systems can be used, including amplification assays, such as PCR, basic probe hybridization assays, and so forth. The antibodies, such as polyclonal antibodies, monoclonal antibodies, the hybridomas which produce them, recombinantly produced antibodies, binding fragments of these, hybridization kits, DNA probes, and so forth, are all additional features of the invention.

Any of these assays can also be used in progression/regression studies. Since it is clear that a low or non-existent level of expression of SCP protein is found in normal cells, one can monitor the course of abnormality involving expression of SCP, simply by monitoring levels of the protein, its expression, and so forth using any or all of the methods set forth supra.

It should be clear that these methodologies may also be used to track the efficacy of a therapeutic regime. Essentially, one can take a baseline value for the SCP protein or proteins being tested, using any of the assays discussed supra, administer a given therapeutic agent, and then monitor levels of the protein thereafter, observing changes in SCP levels as indicia of the efficacy of the regime. Further approaches to this aspect of the invention, inter alia, detection of T cells which recognize SCP 3 or complexes of SCP3 derived peptides and MHC molecules, via $^{51}$Cr release, TNF production, ELISPOT, or by the use of soluble multimeric complexes of peptides and MHC molecules.

The identification of SCP proteins as being implicated in pathological conditions such as cancer also suggests a number of therapeutic approaches to such conditions. The experiments set forth supra establish that antibodies are produced in response to expression of the protein, suggesting its use as a vaccine. Hence, a further embodiment of the invention is the treatment of conditions which are characterized by aberrant or abnormal levels of one or more SCP proteins, via immunotherapeutic approaches. One of these approaches is the administration of an amount of an SCP protein, or an immunogenic peptide derived from the protein in an amount sufficient to provoke or augment an immune response. The protein or peptide may be combined with one or more of the known immune adjuvants, such as saponins, GM-CSF, interleukins, and so forth. If the peptides are too small to generate a sufficient antibody response, they can be coupled to the well known conjugates used to stimulate responses.

Similarly, the immunotherapeutic approaches include administering an amount of inhibiting antibodies sufficient to inhibit the SCP protein. These antibodies may be, e.g., antibodies produced via any of the standard approaches elaborated upon supra.

T cell responses may also be elicited by using peptides derived from the SCP proteins which then complex, non-covalently, with MHC molecules, thereby stimulating proliferation of cytolytic and helper T cells against any such complexes in the subject. It is to be noted that the T cells may also be elicited in vitro using immune responsive cells such as dendritic cells, lymphocytes, or any other immune responsive cells, and then reperfused into the subject being treated.

Note that the generation of T cells and/or antibodies can also be accomplished by administering cells, preferably treated to be rendered non-proliferative, which present relevant T cell or B cell epitopes for response. These may be treated to present the peptide via pulsors, or transformation/transfections to express the peptide.

The therapeutic approaches may also include gene therapies, wherein an antisense molecule, preferably from 10 to 100 nucleotides in length, is administered to the subject either "neat" or in a carrier, such as a liposome, to facilitate incorporation into a cell, followed by inhibition of expression of the protein. Such antisense sequences may also be incorporated into appropriate vaccines, such as in viral vectors (e.g., Vaccinia), bacterial constructs, such as variants of the well known BCG vaccine, and so forth.

An additional DNA based therapeutic approach is the use of a vector which comprises one or more nucleotide sequences, preferably a plurality of these, each of which encodes an immunoreactive peptide derived from the expressed proteins. One can combine these peptide expressing sequences in all possible variations, such as one from each protein, several from one or more protein and one from each of the additional proteins, a plurality from some and none from others, and so forth.

Other features of the invention will be clear to the skilled artisan, and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. Isolated nucleic acid molecule which encodes a protein that is encoded by an isolated nucleic acid molecule comprising SEQ ID NO: 1, 2, 4 or 7.

2. The isolated nucleic acid molecule of claim 1, which encodes a human SCP-3 protein.

3. The isolated nucleic acid molecule of claim 1, wherein said isolated nucleic acid molecule has a nucleotide sequence consisting of SEQ ID NO: 1, SEQ ID NO: 2, SEQ ID NO: 4, or SEQ ID NO: 7.

4. An isolated nucleic acid molecule consisting of a nucleotide sequence set forth in any of SEQ ID NOS: 5, 6, 8, 9, 11, 13 or 14.

5. Recombinant cell which comprises the isolated nucleic acid molecule of claim 1.

6. Expression vector comprising the isolated nucleic acid molecule of claim 1, operably linked to a promoter.

7. Recombinant cell comprising the expression vector of claim 6.

8. Isolated nucleic acid molecule consisting of a nucleotide sequence which encodes a protein that is encoded by Seq ID No.4.

* * * * *

SEQUENCE LISTING

<160> NUMBER OF SEQ ID NOS: 15

<210> SEQ ID NO 1
<211> LENGTH: 1116
<212> TYPE: DNA
<213> ORGANISM: Homo sapiens

<220> FEATURE:

<400> SEQUENCE: 1

| | | | | | |
|---|---|---|---|---|---|
| aggaagtcct | gcctgcagct | ctcacgagaa | ctgaggaccc | gttttcttta | cttttctttt | 60 |
| tttttgtttt | tttgttttgt | tttttttggg | acggagtctg | gctcttgctg | cctaggctgc | 120 |
| agtgcagtgg | tgtgatctgg | gctcactgca | acctccgcct | cctgggttca | agcaattctc | 180 |
| ctgcctcagc | ttcctgagag | acccgttttt | ctaagaggtc | ctagtggtgc | cgctgcctgc | 240 |
| aggttctttg | agggcgccac | atcagggggtc | cctcaggttc | ggggatcgcc | tctagcttcc | 300 |
| caggacaacc | agccacggat | cctgtgggca | ggagggctgc | caaggcccag | ttggaggctc | 360 |
| aatttatggc | ggcctggggg | aagaagcatg | caggaaagga | tccagtccgt | gatgaatgtg | 420 |
| aggaaagaaa | ccgttttaca | gaaacaaggg | aggaagatgt | aactgatgag | catggggaaa | 480 |
| gagaacctttt | tgctgaaaca | gatgaacaca | cgggggctaa | taccaagaag | ccagaagata | 540 |
| ctgcagagga | tcttactgca | aaaagaaaaa | ggatgaaaat | ggataaaact | tgcagcaaaa | 600 |
| caaagaacaa | aagtaaacat | gctttgagaa | aaaagcaact | taaaaggcag | aaacgtgatt | 660 |
| atatacattc | tctgaagttg | ctaaatgtcc | ttgaagaata | catcacagac | gagcagaaag | 720 |
| aggaagaaga | agaagaggga | gaagaggaag | aactaattag | aatatttcaa | gaacaacaga | 780 |
| agaagtggca | acaatataga | agtgttagga | gagagaggct | gaaagagatg | aagctgctac | 840 |
| gtgaccaatt | cgtaaaggct | cttgaggact | ttgaagaccct | ttgtgacaga | gttttttccg | 900 |
| atgaagacag | tgaacttgat | aactagacat | gtttttaaat | aaaatcatgt | cagaactctt | 960 |
| ttggaaaagt | tggcacttac | ccagttgtct | cttcaacctc | tgttattctg | atgactgaag | 1020 |
| aaagaacttg | aacctatgtt | atatgataca | agcacaactt | gagctacagt | aaactacatg | 1080 |
| acagtgtttt | gataattgtt | gtataaatcg | gtatag | | | 1116 |

<210> SEQ ID NO 2
<211> LENGTH: 1276
<212> TYPE: DNA
<213> ORGANISM: Homo sapiens
<220> FEATURE:

<400> SEQUENCE: 2

| | | | | | |
|---|---|---|---|---|---|
| gcctgcaggt | tctgtgagga | agcggcatca | ggggtccctc | aggttcaggg | atcgcctcta | 60 |
| acttcccagg | acagccaacc | atggagcccg | tgggcaggaa | gcgcagcagg | aaggctgcca | 120 |
| aagctcagtt | ggaagctcaa | gttacggccg | cccagggggc | cacgaaagaa | ggttcaggga | 180 |
| tcgcctctaa | cttcccagga | cagccaacca | tggagcccgt | gggcaggaag | cgcagcagga | 240 |
| aggctgccaa | agctcagttg | gaagctcaag | ttagggccgc | cccggcgaag | aagcacacag | 300 |
| gaaaggatcc | agtccgtgat | gaatgtgagg | aaagaaaccc | ttttacagaa | acaagggagg | 360 |
| aagatgtaac | ttatgagcat | ggggaaagag | aaccttttgc | tgaaaaagat | gaacacacgg | 420 |
| ggattcatac | catgaagcta | gaacatattg | cagctgacat | tcaaaagggc | cttgctgcaa | 480 |
| aaagagaaat | gataaaaata | gataaagcag | cttacaggaa | aaccaagaac | acaattgaac | 540 |
| gtgctttgat | aaaaaaacaa | ctaaaaaggc | agaaacgtga | ttatagacat | actcggaagt | 600 |
| tgctgaatgt | ccttaaagaa | tacatcgcag | agaagcagaa | agatgatgaa | gcagaagaag | 660 |
| cagaagccgc | agcagcagca | gcggaagccg | cagcagcagc | agaagccgca | gcagcagcag | 720 |
| cagaagtaat | agtagtagaa | gacgaagagg | aggaagagaa | ggaggaggag | gagagaaag | 780 |
| aagaggagga | agaagaagga | gaagaagaag | gaggaggaga | agaaggagaa | gaaggaggag | 840 |

-continued

| | |
|---|---|
| gaggaggaga aggagaagaa acagaagaag aggaagagga agaagaagaa gaggaagagg | 900 |
| aagaacaaat taaagcattt caagaaaaac agaagaggtg gcaacaacct acaggtgtta | 960 |
| ggagctggag gctgagagag atgaagccgc tacttgagca attactaaag gctgccaagg | 1020 |
| acactaaaga caattattgc atcatttctt ccagtgaaga aagtgaactt gataactagc | 1080 |
| cgtgttttta aaagaatcg tgtcagaact cttttggaag agttggcact tcattgtctc | 1140 |
| ttcaacctct gttattctga tgactgaaga aagaacttga acctatgtta tatgatacga | 1200 |
| gcacaacttg agctacagta aactacatga cagtgttttg ataattgttg tataaatcgg | 1260 |
| tatagctcct ctgtca | 1276 |

<210> SEQ ID NO 3
<211> LENGTH: 320
<212> TYPE: DNA
<213> ORGANISM: Homo sapiens
<220> FEATURE:

<400> SEQUENCE: 3

| | |
|---|---|
| aatatttcaa gagcaacaaa agagacggca acaagatggg aaaggaactg aaagagattg | 60 |
| agccgccaca tgagcaattc acaaaggtct gaggacttgg aagagtataa tgaaagccct | 120 |
| cttttggtg aagaaagtgg taaatttctt tttttgagac aactgcagta agagttggca | 180 |
| cttattcaga tgtctcttta accactgtta ttctgatggc tgatgaaaaa acttgaacct | 240 |
| atgttatatg atacaagcat aacttgagct acactaaacc acatgacagt atttagttaa | 300 |
| ttctcgtata aattagtgta | 320 |

<210> SEQ ID NO 4
<211> LENGTH: 485
<212> TYPE: DNA
<213> ORGANISM: Homo sapiens
<220> FEATURE:

<400> SEQUENCE: 4

| | |
|---|---|
| ggttcagagg tcgcctctag cttcccaggc cagtcagcca cggagcccgt gggcaggaag | 60 |
| ggcagcagga tggctgccaa ggaccagttg gaggttcaag ttatggccgc ccaggaaatg | 120 |
| gagcttgcag gaaaggatcc agtaagtcat gagcatgagg aaagaaaacc tgttacagag | 180 |
| acaaaggagg gagatgtaac tgatgagcat ggggaaagag gatcttttgc tgaaacagat | 240 |
| gaacacacgg gggttgatac caaggagcta gaagatattg cagctgacat taagagcat | 300 |
| cttgctgcaa agagaaaaag gattgaaaag attgcaaaag cttgcagcga aataaagaac | 360 |
| agaattaaaa atgttttgag aacaacacaa ctaaaaaggc agaaacgtga ttatagaatt | 420 |
| tctctgaagt tgccgaatgt ccttgaagag ttcatcacag atgagcagaa agatgaggaa | 480 |
| ggaga | 485 |

<210> SEQ ID NO 5
<211> LENGTH: 24
<212> TYPE: DNA
<213> ORGANISM: Homo sapiens
<220> FEATURE:

<400> SEQUENCE: 5

| | |
|---|---|
| acagaagtgt ctaggattca ttca | 24 |

<210> SEQ ID NO 6
<211> LENGTH: 21
<212> TYPE: DNA

<213> ORGANISM: Homo sapiens
<220> FEATURE:

<400> SEQUENCE: 6
gaagaggtgg caacaatata g                                           21

<210> SEQ ID NO 7
<211> LENGTH: 407
<212> TYPE: DNA
<213> ORGANISM: Homo sapiens
<220> FEATURE:

<400> SEQUENCE: 7
cagtgaattg taatacgact cactataggg cgaattgggc cctctagatg catgctcgag    60
cggccgccag tgtgatggat atctgcagaa ttcggcttga agaggtggca acaatatagc   120
attgttagga gacagcaaat gaaagagatt aagctgctat atgagcaatt cacgaagagt   180
atcatgaaag aactcttttc agtgaagaaa gtcaatttaa atcgccaagt tccaagataa   240
aattgtgtga gagacactgc agcaagagtt ggcactaatt cataacttga gctacactaa   300
accacatgac agtattttga tattcttgta taaaccagtt tatttcttct atcattagtc   360
tgttaaatgc cagacctcat ttctgtggtc tgttaatga atcctag                 407

<210> SEQ ID NO 8
<211> LENGTH: 21
<212> TYPE: DNA
<213> ORGANISM: Homo sapiens
<220> FEATURE:

<400> SEQUENCE: 8
acctacaggt gttaggagct g                                           21

<210> SEQ ID NO 9
<211> LENGTH: 21
<212> TYPE: DNA
<213> ORGANISM: Homo sapiens
<220> FEATURE:

<400> SEQUENCE: 9
acagaggttg ttgagacaat g                                           21

<210> SEQ ID NO 10
<211> LENGTH: 21
<212> TYPE: DNA
<213> ORGANISM: Homo sapiens
<220> FEATURE:

<400> SEQUENCE: 10
gcagaaacgt gattatagaa t                                           21

<210> SEQ ID NO 11
<211> LENGTH: 21
<212> TYPE: DNA
<213> ORGANISM: Homo sapiens
<220> FEATURE:

<400> SEQUENCE: 11
ggttgaagat acatctgaat a                                           21

<210> SEQ ID NO 12
<211> LENGTH: 4967
<212> TYPE: DNA
<213> ORGANISM: Homo sapiens

<220> FEATURE:

<400> SEQUENCE: 12

| | | | | | |
|---|---|---|---|---|---|
| aaatgaagtc | aaaatgccaa | taagaccaga | tctccagcag | ttggaaaaat | gcattgatga | 60 |
| tgctttaaga | aaaatgatt | tcaaacctt | gaaacactt | ttgcaaattg | atatttgtga | 120 |
| agatgtgaag | attaaatgca | gcaaacagtt | tttccacaag | gtggacaacc | ttatatgcag | 180 |
| ggaacttaat | aaagaggata | tccacaatgt | ttcagccatt | ttggtttctg | ttggaagatg | 240 |
| tggcaaaaat | atcagtgtat | tggggcaagc | tggacttcta | acgatgataa | aacaaggact | 300 |
| aatacaaaag | atggttgcct | ggtttgaaaa | atccaaggac | attattcaga | gtcaaggaaa | 360 |
| ttcaaaagat | gaagctgttc | taaatatgat | agaagactta | gttgatcttc | tgctggtcat | 420 |
| acatgatgtc | agtgatgaag | gtaaaaaaca | agtagtggaa | agtttcgtac | ctcgcatttg | 480 |
| ttccctggtt | attgactcaa | gagtgaatat | ttgtattcag | caagagatta | taaaaaaat | 540 |
| gaatgctatg | cttgacaaaa | tgcctcaaga | tgcccggaaa | atactctcta | accaagaaat | 600 |
| gttaattctc | atgagtagta | tgggagaaag | gatttagat | gctggagatt | atgacttaca | 660 |
| ggtagccatt | gtagaagctt | tgtgtagaat | gaccacagaa | aaacaaagac | aagaactggc | 720 |
| acatcagtgg | ttttcaatgg | attttattgc | taaggcattt | aaaagaatta | aggactctga | 780 |
| atttgaaaca | gattgcagga | tatttctcaa | ccttgtaaat | ggcatgcttg | gagacaaaag | 840 |
| aagggtcttt | acatttcctt | gtttatcagc | atttcttgat | aaatatgagc | tgcaaatacc | 900 |
| atcagatgaa | aaacttgagg | aattttggat | tgatttaat | cttgggagtc | agactctctc | 960 |
| attctacatt | gctggagata | atgatgatca | tcaatgggaa | gcagttactg | tgccagagga | 1020 |
| aaaagtacaa | atatacagca | ttgaagtgag | agaatcaaag | aagctactga | caataattct | 1080 |
| gaaaatacaa | gtaaaatta | gcaaagaga | agggaaagaa | ttgcttttgt | atttttgacgc | 1140 |
| atcactagaa | atcactaatg | taactcaaaa | aatttttggt | gcaactaaac | atagggaatc | 1200 |
| tatcagaaaa | caaggtattt | cagttgccaa | aacgtcgctg | catatacttt | ttgacgcaag | 1260 |
| tggatcacag | attctagtgc | cagaaagtca | aatctcacca | gtcggagaag | agctcgttag | 1320 |
| tttaaaggaa | aaatcaaagt | ccccaaagga | atttgctaaa | ccttcaaaat | atatcaaaaa | 1380 |
| cagtgacaaa | gggaatagaa | ataatagtca | gcttgagaaa | actactccta | gcaaaagaaa | 1440 |
| aatgtctgaa | gcatcaatga | ttgtttctgg | tgcagataga | tacactatga | gaagtccagt | 1500 |
| gcttttcagc | aacacatcaa | taccaccacg | aagaagaaga | attaaaccac | cactgcaaat | 1560 |
| gacgagctct | gcagagaaac | ctagtgtttc | tcaaacatca | gaaaatagag | tggataatgc | 1620 |
| tgcatcactg | aaatctagat | catcagaagg | aagacataga | agagataata | tagacaaaca | 1680 |
| tatcaaaact | gctaagtgtg | tagaaaacac | agaaaataag | aatgttgaat | tcccaaacca | 1740 |
| aaattttagt | gaactccagg | atgttatacc | agattcacag | gcagcggaaa | aaagagatca | 1800 |
| tactatatta | cctggtgttt | tagacaacat | ctgtggaaat | aaaatacaca | gcaaatgggc | 1860 |
| atgttggaca | cctgtaacaa | acattgaact | atgtaataac | caaagagcaa | gtacttcgtc | 1920 |
| aggagacaca | ttgaatcaag | atattgttat | aaataaaaaa | cttactaaac | aaaaatcatc | 1980 |
| ctcttcaata | tctgatcata | attctgaagg | aacaggaaaa | gtgaaatata | agaaagaaca | 2040 |
| aaccgaccat | atcaaaatag | ataaagcaga | agtagaagtt | tgcaggaaac | acaatcagca | 2100 |
| acaaaatcat | cctaaatatt | cagggcagaa | aaatactgaa | aatgccaagc | agagtgattg | 2160 |
| gcctgttgaa | tctgaaacta | cttttaaatc | ggttctccta | aataagacaa | ttgaagaatc | 2220 |
| gctgatatat | aggaagaaat | acatattgtc | aaaagatgtg | aatactgcta | cttgcgataa | 2280 |

-continued

```
aaatccatct gctagcaaaa atgtgcaaag tcatagaaaa gcagagaaag aattgacttc    2340
tgagcttaat tcctgggatt cgaaacaaaa aaaatgaga gaaaagtcaa aagggaaaga    2400
atttaccaat gtagcagaat ccttgataag ccaaatcaat aaaagataca aaacaaaaga    2460
tgacatcaag tctacaagaa aattaaagga gtctttgatt aacagtggtt tttcaaacaa    2520
acctgttgta caactcagta aggaaaaagt tcagaaaaaa agctacagaa aactgaagac    2580
tacctttgtt aatgttactt ctgaatgccc agtgaatgat gtttacaatt ttaatttgaa    2640
tggagctgat gaccctatca taaaacttgg aatccaagag tttcaagcta cagctaaaga    2700
agcttgtgcg gataggtcaa ttagattggt aggtccaagg aatcatgatg aacttaaatc    2760
ttctgtcaaa acaaaagata aaaaaattat aacaaatcat caaagaaaaa atctgtttag    2820
tgatactgaa acagagtaca gatgtgatga cagcaagact gatattagct ggctaagaga    2880
accgaaatca aaaccacagc taatagacta tagcagaaat aaaaatgtga agaatcataa    2940
aagtggaaaa tcaagatcat ccttggaaaa gggacagcca agctctaaaa tgacacccag    3000
taaaaatatc acaaaaaaga tggacaagac aattccggaa ggaagaatca gacttccacg    3060
aaaagcaacc aaaacaaaaa aaaactataa agatctctca aattcagaat cagagtgtga    3120
acaagaattt tcacattcat ttaaagagaa cataccagta aaggaggaga atatccattc    3180
cagaatgaaa acggtaaagc taccaaagaa acaacagaaa gtcttctgtg ctgaaacaga    3240
aaggaactca tcaaaacaat ggaaaaactc atctctacta aaagatgcta tacgagataa    3300
ttgccttgac ttatctccca gatctttatc tggcagtcca tcatctatag aagtaacgag    3360
atgtatagag aaaataacag aaaaggattt tactcaggat tatgactgca taacaaaatc    3420
tatatcacct tatccaaaaa cttcatcact tgaatcctta aatagtaaca gtggagttgg    3480
aggtacaata aagtcaccca aaacaatga gaaaaacttc ctgtgtgcaa gtgaaagttg    3540
ttcaccaact ccacgaccac tgttttttggc cagacatact ccaactaaga gtaatactat    3600
tgtaaataga aaaaaaataa gttctctggt acttacacaa gaaacacaaa acagtaacag    3660
ctattcagat gtaagcagat atagttcaga agaacggttt atggaaattg aatctccaca    3720
tatcaatgaa aattatatac aaagcaaaag agaggaaagt catttagcat cttcattatc    3780
caagtctagt gaaggaagag agaaaacgtg gtttgacatg ccctgtgatg ctactcatgt    3840
atcaggcccc acccaacatc ttagtcgcaa aagaatatat atagaagata atctaagtaa    3900
ttccaatgaa gtagaaatgg aagagaaagg agaaggaga gcaaacttgc ttcccaaaaa    3960
actgtgtaaa attgaagatg cagatcatca tatccacaaa atgtctgaaa gtgtatcttc    4020
attatcaaca aatgactttt ctattccttg ggagacctgg caaaatgaat ttgcagggat    4080
agagatgact tatgagactt acgagaggct caattcagaa tttaagagaa ggaataatat    4140
ccgacataaa atgttgagtt attttactac gcagtcttgg aaaacagctc agcaacatct    4200
gagaacaatg aatcatcaaa gtcaggactc taggattaaa aaacttgata aattccaatt    4260
cattatcata gaggagctgg agaattttga aaaagattca cagtctttaa aagatttgga    4320
aaaggaattt gtggactttt gggaaagat atttcagaag ttcagtgcat atcaaaaaag    4380
cgaacaacag aggcttcatc ttttgaaaac ttcattggct aaaagtgtct tctgtaatac    4440
tgatagtgaa gaaactgttt ttacatccga gatgtgtttg atgaaagaag atatgaaagt    4500
gctgcaagac aggcttctta aggacatgct agaagaggag cttcttaatg tacgcagaga    4560
actgatgtca gtattcatgt ctcatgaaag aaatgctaat gtgtgaaatc tagttttat    4620
```

-continued

```
caccatactt tatctaatta ttattctctg tatataactg aggaaataag aatagtccta    4680
caaagagaaa aatatacatg tcaccgaagc aagtgtaccc tttataggaa ccctcaaatt    4740
aaaaaaaaat gtcttttaat ggatgagagg gaaccactat aacatgagtc caagcccaga    4800
agacttctgt ctatacaata tttttttta attttggaga taaaagcttt aagaaacttt    4860
ttgagttaat tatactcata aaatgagttt ctttaataaa ttaaatttta ttgtgtaaaa    4920
tgtattatta cataaaatgt gtttttgaat caatgcagtt tgggccg                  4967
```

<210> SEQ ID NO 13
<211> LENGTH: 27
<212> TYPE: DNA
<213> ORGANISM: Homo sapiens
<220> FEATURE:

<400> SEQUENCE: 13
gattcggcac gcagggatg ttatacc                                          27

<210> SEQ ID NO 14
<211> LENGTH: 27
<212> TYPE: DNA
<213> ORGANISM: Homo sapiens

<400> SEQUENCE: 14
gccaatcact ctgcttggca ttttcag                                         27

<210> SEQ ID NO 15
<211> LENGTH: 26
<212> TYPE: DNA
<213> ORGANISM: Homo sapiens
<220> FEATURE:

<400> SEQUENCE: 15
gacagaggag ctataccgat ttatac                                          26